(12) United States Patent
Hodges

(10) Patent No.: US 11,650,137 B1
(45) Date of Patent: May 16, 2023

(54) CPAP MACHINE OVERRIDE MONITORING DEVICE

(71) Applicant: Kenneth Hodges, Christiana, TN (US)

(72) Inventor: Kenneth Hodges, Christiana, TN (US)

( * ) Notice: Subject to any disclaimer, the term of this patent is extended or adjusted under 35 U.S.C. 154(b) by 0 days.

(21) Appl. No.: 17/557,209

(22) Filed: Dec. 21, 2021

(51) Int. Cl.
*G01M 99/00* (2011.01)
*A61M 16/00* (2006.01)

(52) U.S. Cl.
CPC ...... *G01M 99/008* (2013.01); *A61M 16/0003* (2014.02); *A61M 2205/70* (2013.01)

(58) Field of Classification Search
CPC ............ G01M 99/008; A61M 16/0003; A61M 2205/70
See application file for complete search history.

(56) References Cited

U.S. PATENT DOCUMENTS

2014/0099621 A1* 4/2014 Fuchs .................. G09B 23/288
434/272

FOREIGN PATENT DOCUMENTS

| CN | 205080823 U | * | 3/2016 | ............. G09B 23/26 |
| CN | 206477133 U | * | 9/2017 | ............. D06B 23/20 |
| KR | 20100047910 A | * | 5/2010 | ........... A61B 5/0035 |

* cited by examiner

*Primary Examiner* — Herbert K Roberts
*Assistant Examiner* — Anthony W Megna Fuentes
(74) *Attorney, Agent, or Firm* — Kyle A. Fletcher, Esq.

(57) ABSTRACT

The CPAP machine override monitoring device comprises an air chamber, a diaphragm, a compression head, a push rod, a connecting rod, a crank, a motor, an ON/OFF control, a speed control, one or more batteries, and an enclosure. The device may be adapted to simulate the inhalations and exhalations of a human such that a CPAP machine coupled to the device may operate without generating an alarm. As a non-limiting example, the device may override the CPAP machine's monitoring of air pressure and/or pressure changes such that the CPAP machine may be tested for extended periods of time. The air chamber may replace a CPAP mask at the end of a CPAP tube. The diaphragm may produce the pressure changes within the air chamber that simulate normal breathing with no leaks.

19 Claims, 4 Drawing Sheets

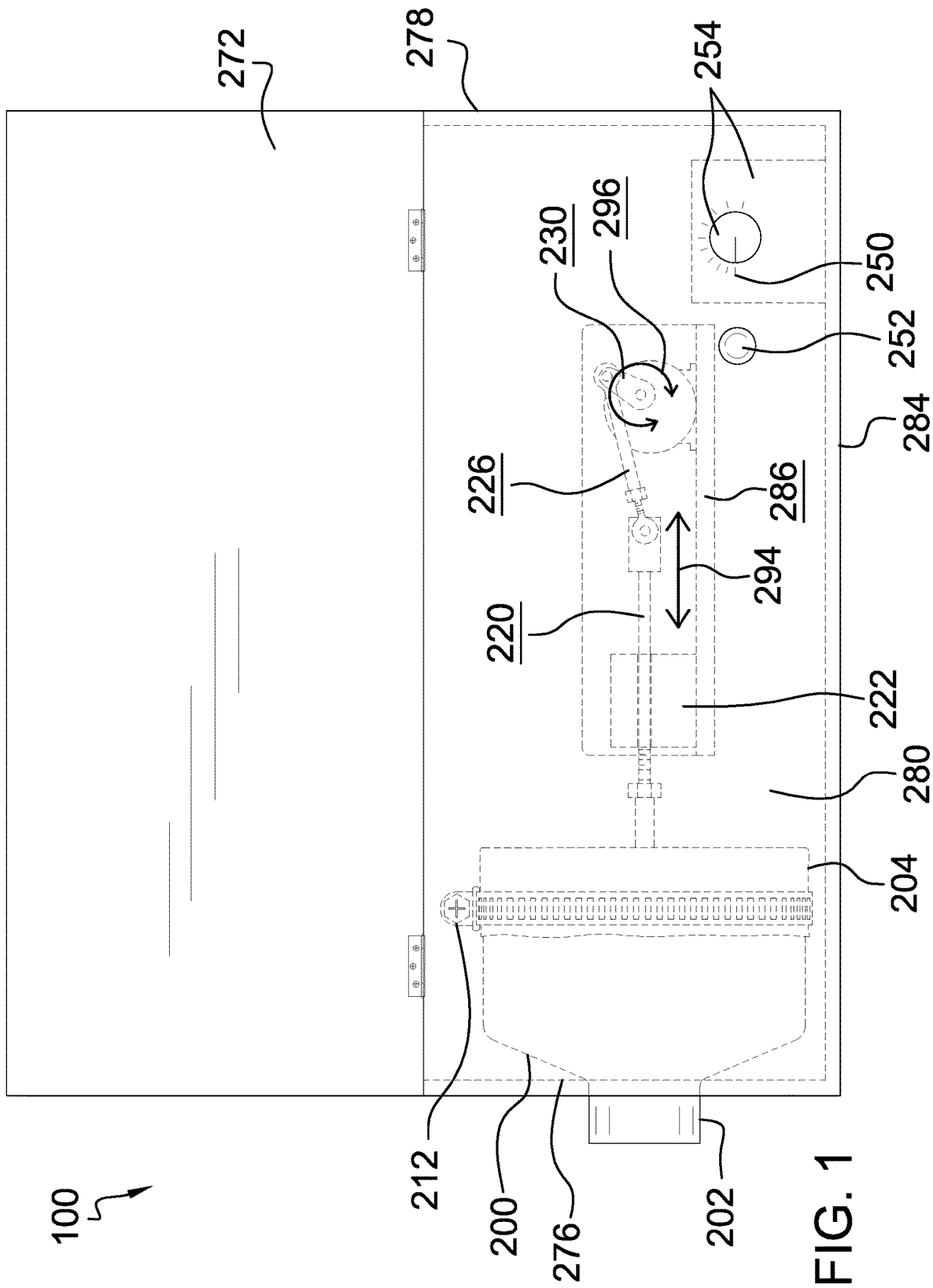

US 11,650,137 B1

CPAP MACHINE OVERRIDE MONITORING DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the fields of CPAP machines and test equipment, more specifically, a CPAP machine override monitoring device.

A CPAP machine may be effective for managing obstructive sleep apnea or other respiratory conditions by continuously applying air pressure greater than atmospheric pressure to the upper respiratory tract of the human. The CPAP machine may monitor the air pressure to determine whether the CPAP machine, a CPAP tube, and a CPAP mask are working properly and may initiate an alarm if there appears to be a problem. As non-limiting examples, an air leak from an ill-fitting mask, cracked tube, or extensively-used CPAP machine may result in pressure anomalies. In some instances, the CPAP machine may monitor not only the air pressure but pressure changes and may initiate an alarm if the pressure changes indicate that a user is not breathing correctly. The alarms may be undesirable when the CPAP machine is being tested for proper operation over an extended period of time.

SUMMARY OF INVENTION

The CPAP machine override monitoring device comprises an air chamber, a diaphragm, a compression head, a push rod, a connecting rod, a crank, a motor, an ON/OFF control, a speed control, one or more batteries, and an enclosure. The device may be adapted to simulate the inhalations and exhalations of a human such that a CPAP machine coupled to the device may operate without generating an alarm. As a non-limiting example, the device may override the CPAP machine's monitoring of air pressure and/or pressure changes such that the CPAP machine may be tested for extended periods of time. The air chamber may replace a CPAP mask at the end of a CPAP tube. The diaphragm may produce the pressure changes within the air chamber that simulate normal breathing with no leaks.

An object of the invention is to simulate inhalations and exhalations of a human while the invention is coupled to a CPAP machine via a CPAP tube.

Another object of the invention is to provide an air chamber with a diaphragm to simulate the upper respiratory tract of the human.

A further object of the invention is to move a compression head against the diaphragm in a reciprocating motion to simulate breathing.

Yet another object of the invention is to provide a speed control to vary the simulated breathing rate.

These together with additional objects, features and advantages of the CPAP machine override monitoring device will be readily apparent to those of ordinary skill in the art upon reading the following detailed description of the presently preferred, but nonetheless illustrative, embodiments when taken in conjunction with the accompanying drawings.

In this respect, before explaining the current embodiments of the CPAP machine override monitoring device in detail, it is to be understood that the CPAP machine override monitoring device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the CPAP machine override monitoring device.

It is therefore important that the claims be regarded as including such equivalent construction insofar as they do not depart from the spirit and scope of the CPAP machine override monitoring device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 1 is a front view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 3:
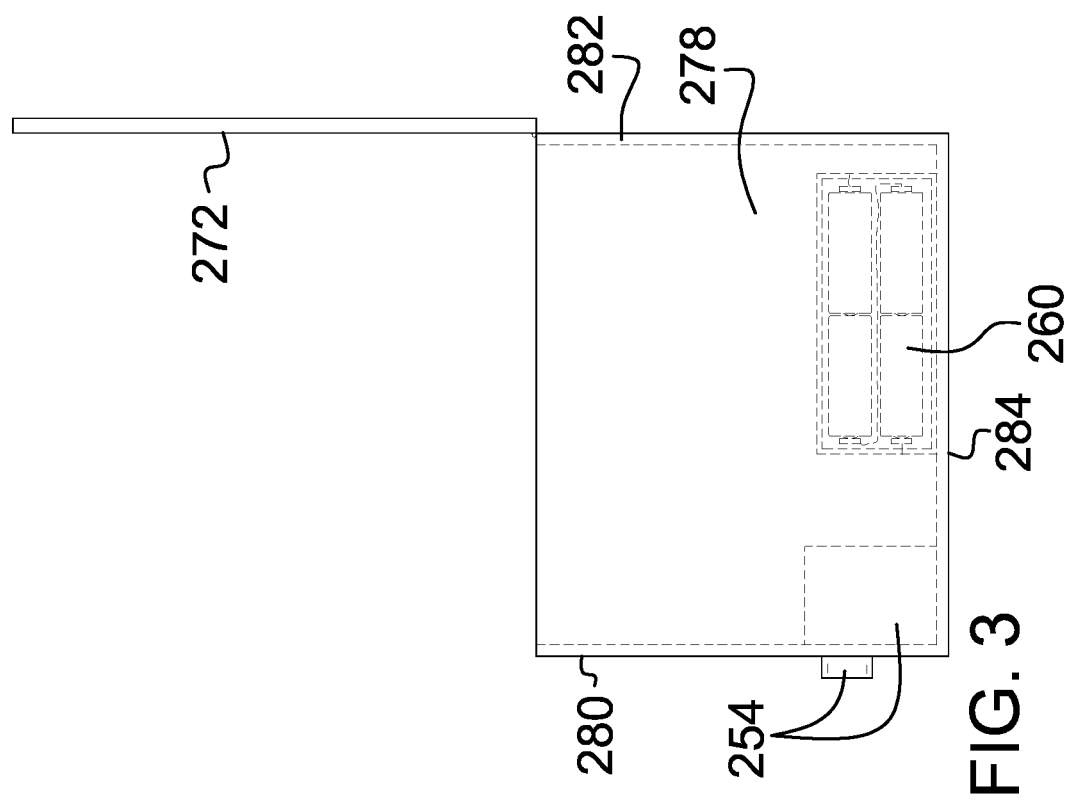
FIG. 3 is a right side view of an embodiment of the disclosure.
Figure 2:
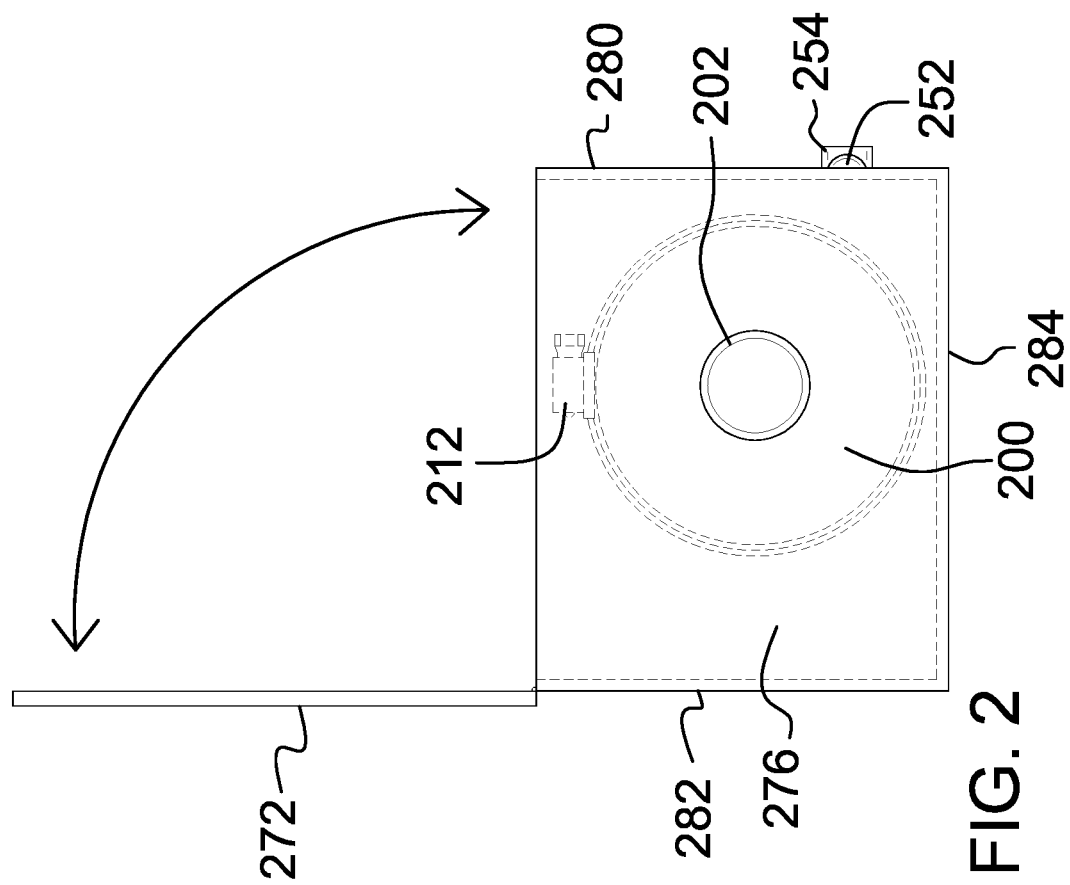
FIG. 2 is a left side view of an embodiment of the disclosure.
Figure 4:
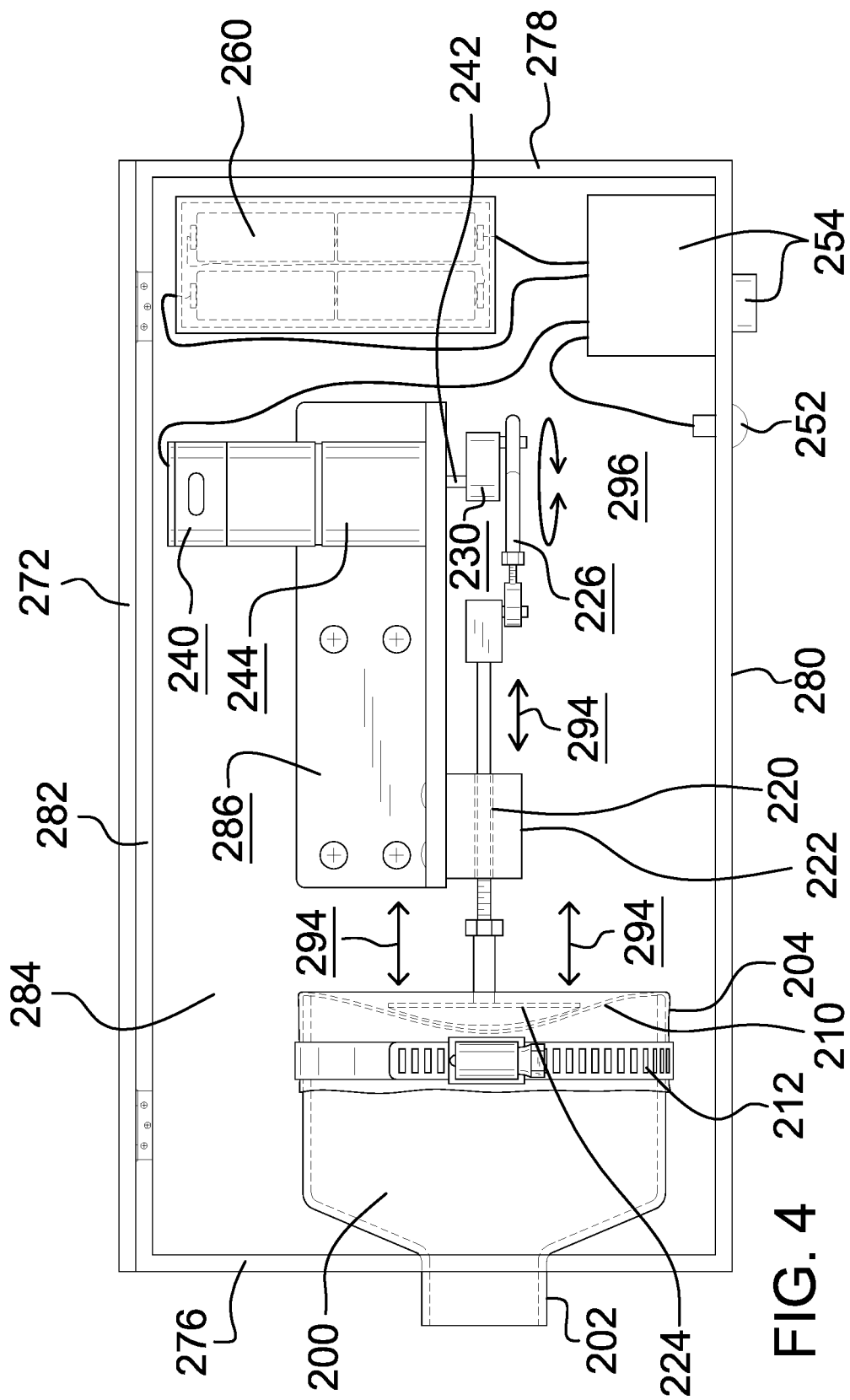
FIG. 4 is a top view of an embodiment of the disclosure with the lid open.
Figure 5:
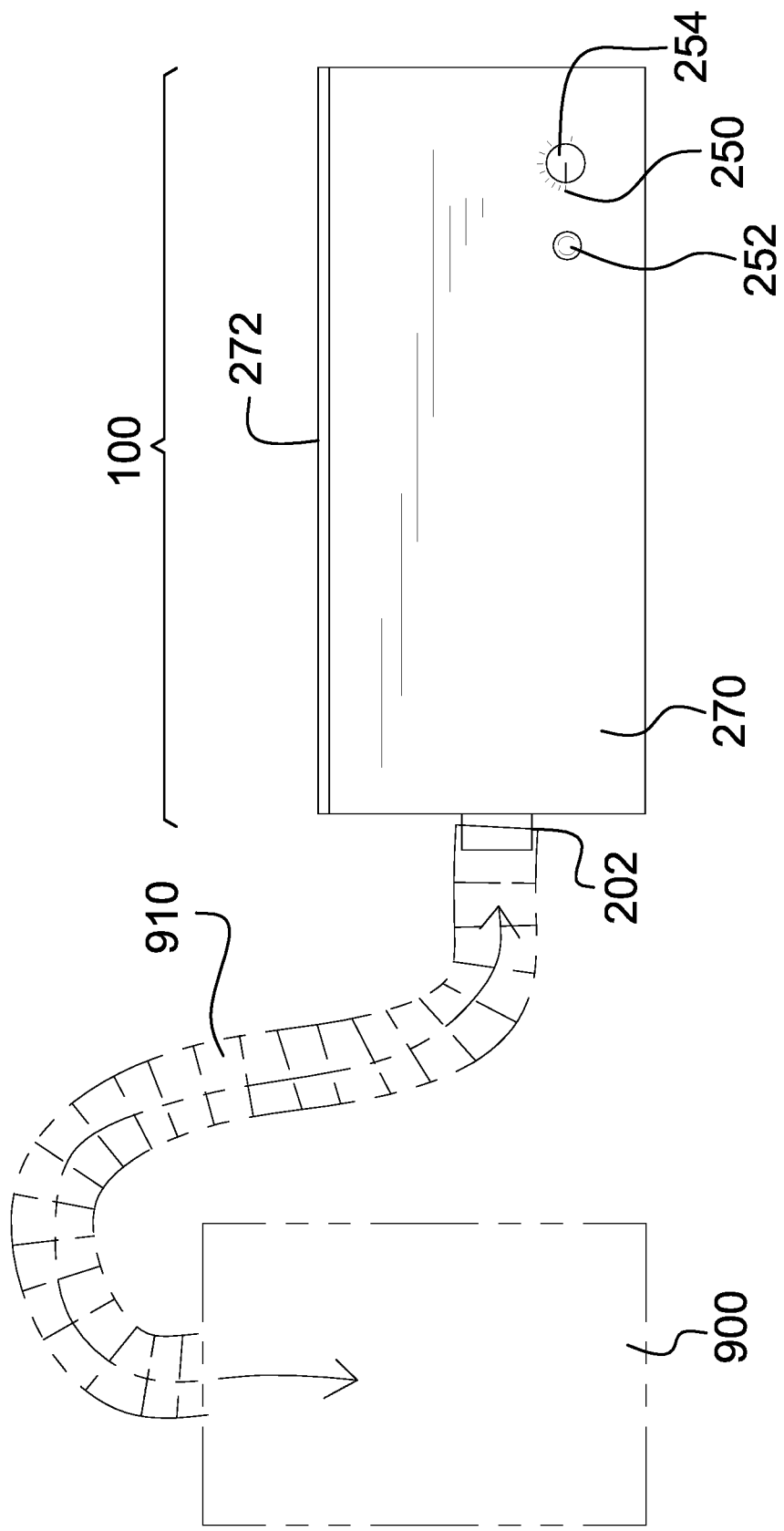
FIG. 5 is an in-use view of an embodiment of the disclosure illustrating the device coupled to a CPAP machine via a CPAP tube.

Detailed reference will now be made to a first potential embodiment of the disclosure, which is illustrated in FIGS. 1 through 5.

The CPAP machine override monitoring device 100 (hereinafter invention) comprises an air chamber 200, a diaphragm 210, a compression head 224, a push rod 220, a connecting rod 226, a crank 230, a motor 240, an ON/OFF control 250, a speed control 254, one or more batteries 260, and an enclosure 270. The invention 100 may be adapted to simulate the inhalations and exhalations of a human such that a CPAP machine coupled to the invention 100 may operate without generating an alarm. As a non-limiting example, the invention 100 may override the CPAP machine's monitoring of air pressure and pressure changes such that the CPAP machine 900 may be tested for extended periods of time. The air chamber 200 may replace a CPAP mask at the end of a CPAP tube 910. The diaphragm 210 may produce the pressure changes within the air chamber 200 that simulate normal breathing with no leaks.

The air chamber 200 may be a cylindrical plenum comprising a narrow end 202 and a wide end 204. The narrow end 202 may be exposed externally at one of a side of the enclosure 270 where the CPAP tube 910 may detachably couple to the air chamber 200. The wide end 204 may be located inside of the enclosure 270 and may be covered by the diaphragm 210. The narrow end 202 may have a diameter that corresponds to the diameter of the CPAP tube 910 that may couple to the air chamber 200. The diameter of the wide end 204 may be greater than the diameter of the narrow end 202. The interior of the air chamber 200 may be pressurized by the CPAP machine 900 via the CPAP tube 910. Movement of the diaphragm 210 may change the air pressure within the air chamber to simulate breathing. The CPAP machine 900 may sense the pressure changes caused by movement of the diaphragm 210 and may interpret the pressure changes as normal breathing by a person using the CPAP machine 900.

The diaphragm 210 may be flexible elastic membrane that may cover the wide end 204 of the air chamber 200. As non-limiting examples, the diaphragm 210 may be a natural or synthetic rubber membrane. Movement of the diaphragm 210 may change the volume of the air chamber 200 and may therefore alter the air pressure within the air chamber 200. Increasing the air pressure within the air chamber 200 may simulate exhalation from the perspective of the CPAP machine 900. In a preferred embodiment, the diaphragm 210 may be held in placed by a clamp that surrounds the wide end 204 of the air chamber 200. The clamp 212 may be removable for replacement of the diaphragm 210.

The compression head 224 may be a semi-spherical plunger that may press against the center of the diaphragm 210 from the outside of the air chamber 200. The compression head 224 may move in a reciprocating motion 294 to increase the air pressure within the air chamber 200 by pushing the diaphragm 210 into the air chamber 200 and to decrease the air pressure within the air chamber 200 by relaxing the diaphragm 210.

A first end of the push rod 220 may be coupled to the compression head 224 and a second end of the push rod 220 may be pivotably coupled to the connecting rod 226. The push rod 220 may move the compression head 224 in the reciprocating motion along the centerline of the air chamber 200. The push rod may be guided by a push rod guide 222.

A first end of the connecting rod 226 may be pivotably coupled to the push rod 220 and a second end of the connecting rod 226 may be pivotably coupled to the crank 230. The connecting rod 226 may convert rotational motion 296 of the crank 230 into the reciprocating motion 294 of the push rod 220. The crank 230 may be an armature that may convey the rotational motion 296 of a gearbox output 248 to the connecting rod 226.

The motor 240 may convert electrical energy into mechanical energy. The motor 240 may cause the rotational motion of a motor shaft 242 when the electrical energy is applied to the motor 240. The electrical energy applied to the motor 240 may be controlled by the ON/OFF control 250 and the speed control 254. The motor shaft 242 may be coupled to a gearbox input.

A gearbox 244 may couple the motor shaft 242 to the crank 230. The gearbox 244 may be an enclosed set of gears that may convert rotational speed and torque between the gearbox input and the gearbox output. The gearbox input may be coupled to the motor shaft 242 and the gearbox output may be coupled to the crank 230. The gearbox 244 may convert the rotational speed of the motor 240 such that the crank 230 turns at 10 to 80 revolutions per minute. 10 to 80 revolutions per minute may result in a movement of the diaphragm 210 that simulates normal breathing.

The ON/OFF control 250 may energize the motor 240 when the ON/OFF control 250 is in an ON position and may deenergize the motor 240 when the ON/OFF control 250 is on an OFF position. An ON/OFF indicator 252 may indicate the power state of the invention 100. The ON/OFF indicator 252 may illuminate when the ON/OFF control 250 is in the ON position and may extinguish when the ON/OFF control 250 is in the OFF position. The speed control may control the rotational speed of the motor 240 and may therefore control the timing of the diaphragm 210 movements.

In some embodiments, the ON/OFF control 250, the ON/OFF indicator 252, the speed control 254, or combinations thereof may be packaged as a single unit. As non-limiting examples, the ON/OFF control 250 and the ON/OFF indicator 252 may be combined into a single control, the ON/OFF control 250 and the speed control 254 may be combined into a single rotary control where a speed of 0 corresponds to the OFF position, or the ON/OFF control 250, the ON/OFF indicator 252, and the speed control 254 may be combined into a single rotary control where a speed of 0 corresponds to the OFF position and the rotary control illuminates when the motor 240 is energized.

The one or more batteries 260 may comprise one or more energy-storage devices. The one or more batteries 260 may be a source of electrical energy to operate the motor 240. The one or more batteries 260 may be rechargeable and/or replaceable.

The enclosure 270 may be a protective cover for the invention 100. The enclosure 270 may prevent injuries by shielding moving parts and electrical components. The enclosure may comprise a left side 276, a right side 278, a front panel 280, a rear panel 282, a bottom panel 284, and a lid 272. In a preferred embodiment, the ON/OFF control 250, the ON/OFF indicator 252, and the speed control 254 are accessible on the front panel 280 and the narrow end 202 of the air chamber 200 is accessible on either the left side 276 or the right side 278.

The lid 272 may be hingedly coupled to the rear panel 282 of the enclosure 270. The lid 272 may open to provide access to the mechanical components and electronics container within the enclosure 270 and may close to prevent access to the interior of the enclosure 270. When closed, the lid 272 may be retained by a latch to prevent opening.

The enclosure 270 may comprise a motor-mounting bracket to support the motor 240 and the push rod guide 222. The motor-mounting bracket 286 may be coupled to the interior of the enclosure 270.

In use, the CPAP mask may be removed from the CPAP machine and the CPAP tube 910 may be detachably coupled to the narrow end 202 of the air chamber 200 where the narrow end 202 of the air chamber 200 is exposed on the side of the enclosure 270. The CPAP machine 900 may be turned on and the ON/OFF control 250 on the invention 100 may be moved to the ON position to energize the motor 240 and to begin the reciprocating motion of the compression head 224 against the diaphragm 210. The CPAP machine 900 may produce pressure positive air pressure within the air chamber 200 by pressurizing the interior of the air chamber 200 to a pressure above atmospheric. As the compression head 224 flexes and relaxes the diaphragm 210, the CPAP machine 900 may sense the pressure changes and may interpret the pressure changes as normal human breathing as if the CPAP tube 910 were coupled to the CPAP mask with a human breathing into the CPAP mask. The speed control 254 may be varied to change the simulated breathing rate.

Definitions

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" may refer to top and "lower" may refer to the bottom. As a non-limiting example, the upper end of a vertical shaft is the top end of the vertical shaft.

Throughout this document the terms "battery", "battery pack", and "batteries" may be used interchangeably to refer to one or more wet or dry cells or batteries of cells in which chemical energy is converted into electricity and used as a source of DC power. References to recharging or replacing batteries may refer to recharging or replacing individual cells, individual batteries of cells, or a package of multiple battery cells as is appropriate for any given battery technology that may be used. The battery may require electrical contacts which may not be illustrated in the figures.

As used in this disclosure, the "centerline" may be an imaginary line that defines the center of one or more cross sections of an object. Unless stated otherwise, the centerline follows a longitudinal path through the object at the center of lateral cross sections. If the object is tubular, the centerline follows the center of the tube.

As used herein, the words "control" or "controls" are intended to include any device which can cause the completion or interruption of an electrical circuit; non-limiting examples of controls include toggle switches, rocker switches, push button switches, rotary switches, electromechanical relays, solid state relays, touch sensitive interfaces and combinations thereof whether they are normally open, normally closed, momentary contact, latching contact, single pole, multi-pole, single throw, or multi-throw. In some embodiments, a control may alter an electrical property of a circuit such as resistance, inductance, or capacitance.

As used in this disclosure, the word "correspond" may indicate that a first object is in some manner linked to a second object in a one to one relationship or that one or more properties shared by two or more objects match, agree, or align within acceptable manufacturing tolerances.

As used herein, the words "couple", "couples", "coupled" or "coupling", may refer to connecting, either directly or indirectly, and does not necessarily imply a mechanical connection.

As used herein, "CPAP" may refer to Continuous Positive Airflow Pressure. CPAP may be used as a treatment for obstructive sleep apnea. The continuous positive air flow from a CPAP machine may be applied to the upper respiratory tract of a patient and may prevent the patient's airways from collapsing during sleep.

As used in this disclosure, "elastic" may refer to a material or object that deforms when a force is applied to stretch or compress the material and that returns to its relaxed shape after the force is removed. A material that exhibits these qualities is also referred to as an elastomeric material.

As used herein, "energize" and/or "energization" may refer to the application of an electrical potential to a system or subsystem.

As used herein, "front" may indicate the side of an object that is closest to a forward direction of travel under normal use of the object or the side or part of an object that normally presents itself to view or that is normally used first. "Rear" or "back" may refer to the side that is opposite the front.

As used in this disclosure, a "latch" may be a fastening or locking mechanism. The use of the term latch may imply the insertion of an object into a notch or cavity. The act of latching may involve a linear, pivoting, or rotating motion.

As used in this disclosure, a "motor" may refer to a device that transforms energy from an external power source into mechanical energy.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A CPAP machine override monitoring device comprising:
    an air chamber, a diaphragm, a compression head, a push rod, a connecting rod, a crank, a motor, an ON/OFF control, a speed control, one or more batteries, and an enclosure;
    wherein the CPAP machine override monitoring device is configured to simulate the inhalations and exhalations of a human;
    wherein the air chamber attaches to an end of a CPAP tube;
    wherein the diaphragm produces pressure changes within the air chamber that simulate breathing with no leaks; and wherein the compression head moves in a reciprocating motion to increase air pressure within the air chamber by pushing the diaphragm into the air chamber and to decrease the air pressure within the air chamber by relaxing the diaphragm.

2. The CPAP machine override monitoring device according to claim 1, wherein the air chamber is a cylindrical plenum comprising a narrow end and a wide end; wherein the narrow end is exposed externally at one of a side of the enclosure where the CPAP tube detachably couples to the air chamber; and 2 wherein the wide end is located inside of the enclosure and is covered by the diaphragm.

3. The CPAP machine override monitoring device according to claim 2, wherein the narrow end has a diameter that corresponds to the diameter of the CPAP tube that couples to the air chamber; wherein the diameter of the wide end is greater than the diameter of the narrow end; wherein the interior of the air chamber is pressurized by a CPAP machine via the CPAP tube; and wherein movement of the diaphragm changes air pressure within the air chamber to simulate breathing.

4. The CPAP machine override monitoring device according to claim 3, wherein the diaphragm is flexible elastic membrane that covers the wide end of the air chamber; wherein movement of the diaphragm changes the volume of the air chamber and therefore alters the air pressure within the air chamber; and wherein increasing the air pressure within the air chamber simulates exhalation.

5. The CPAP machine override monitoring device according to claim 4, wherein the diaphragm is held in placed by a clamp that surrounds the wide end of the air chamber; and wherein the clamp is removable for replacement of the diaphragm.

6. The CPAP machine override monitoring device according to claim 4, wherein the compression head is a semi-spherical plunger that presses against the center of the diaphragm from the outside of the air chamber.

7. The CPAP machine override monitoring device according to claim 6, wherein a first end of the push rod is coupled to the compression head and a second end of the push rod is pivotably coupled to the connecting rod; wherein the push rod moves the compression head in the reciprocating motion along the centerline of the air chamber; and wherein the push rod is guided by a push rod guide.

8. The CPAP machine override monitoring device according to claim 7, wherein a first end of the connecting rod is pivotably coupled to the push rod and a second end of the connecting rod is pivotably coupled to the crank; and wherein the connecting rod converts rotational motion of the crank into the reciprocating motion of the push rod.

9. The CPAP machine override monitoring device according to claim 8, wherein the crank is an armature that conveys the rotational motion of a gearbox output to the connecting rod.

10. The CPAP machine override monitoring device according to claim 9, wherein the motor converts electrical energy into mechanical energy; wherein the motor causes the rotational motion of a motor shaft when the electrical energy is applied to the motor; wherein the electrical energy applied to the motor is controlled by the ON/OFF control and the speed control; and wherein the motor shaft is coupled to a gearbox input.

11. The CPAP machine override monitoring device according to claim 10, wherein a gearbox couples the motor shaft to the crank; wherein the gearbox is an enclosed set of gears that converts rotational speed and torque between the gearbox input and the gearbox output; and wherein the gearbox input is coupled to the motor shaft and the gearbox output is coupled to the crank.

12. The CPAP machine override monitoring device according to claim 11, wherein the gearbox converts the rotational speed of the motor such that the crank turns at 10 to 80 revolutions per minute.

13. The CPAP machine override monitoring device according to claim 11, wherein the ON/OFF control energizes the motor when the ON/OFF control is in an ON position and deenergizes the motor when the ON/OFF control is on an OFF position; wherein an ON/OFF indicator indicates the power state of the CPAP machine override monitoring device; wherein the ON/OFF indicator illuminates when the ON/OFF control is in the ON position and does not illuminate when the ON/OFF control is in the OFF position; and wherein the speed control controls the rotational speed of the motor and therefore controls the timing of the diaphragm movements.

14. The CPAP machine override monitoring device according to claim 13, wherein the ON/OFF control, the ON/OFF indicator, the speed control, or combinations thereof are packaged as a single unit.

15. The CPAP machine override monitoring device according to claim 13, wherein the one or more batteries comprise one or more energy-storage devices; wherein the one or more batteries are a source of electrical energy to operate the motor; and wherein the one or more batteries are rechargeable and/or replaceable.

16. The CPAP machine override monitoring device according to claim 15, wherein the enclosure is a protective cover for the CPAP machine override monitoring device; and wherein the enclosure comprises a left side, a right side, a front panel, a rear panel, a bottom panel, and a lid.

17. The CPAP machine override monitoring device according to claim 16, wherein the ON/OFF control, the ON/OFF indicator, and the speed control are accessible on the front panel and the narrow end of the air chamber is accessible on either the left side or the right side.

18. The CPAP machine override monitoring device according to claim 16, wherein the lid is hingedly coupled to the rear panel of the enclosure; and wherein the lid opens to provide access to the mechanical components and electronics contained container within the enclosure and closes to prevent access to the interior of the enclosure.

19. The CPAP machine override monitoring device according to claim 16, wherein the enclosure comprises a motor-mounting bracket to support the motor and the push rod guide; and wherein the motor-mounting bracket is coupled to the interior of the enclosure.

* * * * *